US009771331B2

(12) United States Patent
Kerrison et al.

(10) Patent No.: US 9,771,331 B2
(45) Date of Patent: Sep. 26, 2017

(54) METHODS OF IDENTIFYING NEUROPROTECTIVE COMPOUNDS FOR RETINAL GANGLION CELLS (75) Inventors: John Barnwell Kerrison, Towson, SC (US); Donald J. Zack, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 1653 days.

(21) Appl. No.: 11/918,987

(22) PCT Filed: Apr. 24, 2006

(86) PCT No.: PCT/US2006/015457
§ 371 (c)(1),
(2), (4) Date: Mar. 4, 2009

(87) PCT Pub. No.: WO2006/116301
PCT Pub. Date: Nov. 2, 2006

(65) Prior Publication Data
US 2009/0215765 A1    Aug. 27, 2009

Related U.S. Application Data (60) Provisional application No. 60/674,202, filed on Apr. 22, 2005.

(51) Int. Cl.
| | |
|---|---|
| *G01N 33/50* | (2006.01) |
| *G01N 33/53* | (2006.01) |
| *G01N 33/68* | (2006.01) |
| *C07D 239/50* | (2006.01) |
| *C07C 233/25* | (2006.01) |
| *C07C 239/16* | (2006.01) |
| *C07C 251/86* | (2006.01) |
| *C07C 311/46* | (2006.01) |
| *C07D 207/416* | (2006.01) |
| *C07D 333/22* | (2006.01) |
| *C07D 417/12* | (2006.01) |
| *G01N 33/543* | (2006.01) |
| *G01N 33/569* | (2006.01) |

(52) U.S. Cl.
CPC .......... *C07D 239/50* (2013.01); *C07C 233/25* (2013.01); *C07C 239/16* (2013.01); *C07C 251/86* (2013.01); *C07C 311/46* (2013.01); *C07D 207/416* (2013.01); *C07D 333/22* (2013.01); *C07D 417/12* (2013.01); *G01N 33/5058* (2013.01); *G01N 33/54326* (2013.01); *G01N 33/56966* (2013.01); *C07C 2602/20* (2017.05); *G01N 2800/164* (2013.01)

(58) Field of Classification Search
CPC ............ C12N 2500/99; C12N 2502/13; C12N 2506/02; C12N 5/0606; C12N 5/0623; C12N 5/0619; G01N 2500/00; A61K 2300/00; A61K 35/12
See application file for complete search history.

(56) References Cited

U.S. PATENT DOCUMENTS 3,893,972 A      7/1975  Holt et al.
2004/0228795 A1  11/2004 Bernstein

OTHER PUBLICATIONS

Meyer-Franke et al. Neuron 1995. 15:805-819.*
Huang et al. Invest. Ophthalmol. Vis. Sci. 2003; 44:347-354.*
Ordog et al. Am J. Physiol. Cell Physiol. 2004. 286:C448-C456.*
Jenkins et al. Proteins: structure, Function and Genetics. 2003; 50:81-93.*
Paddison et al. Nature. 2004, 428:427-431.*
Inatani et al. Invest. Ophthalmol. Vis. Sci. 2001; 42:1930-8.*
Takahashi et al. Exp. Eye Res. 1991; 53:565-572.*
Barres et al. Neuroprotocols; 1993; 2:201-204.*
Shoge et al., Neurosci. Lett. 1999; 259:111-114.*
Kerrison et al. Molecular Vision Mar. 15, 2005; 11:208-215.*
Smith et al. Anat Rec. 1988; 222:380-390, abstract.*
Corning culture vessels fact sheet from the corning catalog2002.*
Roux et al. Assay and Drug Development Technologies, 2004; 2: 637-645.*
Wachs et al. Lab. Invest. 2003; 83:949-962.*
Neurobasal fact sheet from the catalog 2002.*
Sandy et al., Biotechnieques, 2005; 39:215-224.*
Anderson et al., "Some Heterocyclic Thiocarbazones," J. Am. Chem. Soc. vol. 73, No. 10 pp. 4967-4968 (1951).
Duca et al., "Experimental tuberculosis. In vivo and in vitro activities of thiosemicarbazones," Chem. Abs. vol. 46 No. 39723 (1952).
Anchan et al., Transforming Growth Factor-β-3 Is Mitogenic for Rat Retinal Progenitor Cells in vitro. J. Neurobiol. 28, 133-45, 1995.
Barres et al., Immunological, Morphological, and Electrophysiological Variation among Retinal Ganglion Cells Purified by Panning, Neuron 1, 791-803, 1988.
Bernstein et al., Analysis of optic nerve stroke by retinal Bex expression. Molecular Vision. 2006: 12:147-155.
Bernstein et al., Functional and Cellular Responses in a Novel Rodent Model of Anterior Ischemic Optic Neuropathy, Invest Ophthalmol Vis Sci 2003; 44:4153-62.
Goldenberg-Cohen et al., Oiigodendrocyte Dysfunction after Induction of Experimental Anterior Optic Nerve Ischemia, Invest Ophthalmol Vis Sci 2005; 46:2716-25.
Guy et al., Adeno-assoclated viral-mediated catalase expression suppresses optic neuritis in experimental allergic encephalomyelitis, Proc. Natl Acad Sci U S A. Nov. 10, 1998;95(23):13847-52.
Ko et al., Dynamic changes in reactive oxygen species and antioxidant levels in retinas in experimenal glaucoma, Free Radic Biol Med. Aug. 1, 2005 39(3):365-73.

(Continued)

Primary Examiner — Chang-Yu Wang
(74) Attorney, Agent, or Firm — Michael Best & Friedrich, LLP; Jeffrey W. Childers (57) ABSTRACT Neuroprotective compounds for treating optic neuropathies and screening methods for identifying neuroprotective compounds.

4 Claims, 5 Drawing Sheets (56) References Cited

OTHER PUBLICATIONS

Leveillard et al., Identification and characterization of rod-derived cone viability factor, Nature Genetics 36, 755-59, 2004.
Liu et al., BMP receptor 1b is required for axon guidance and cell survival in the developing retina. Devel. Biol. 256, 34-48. 2003.
Maier et al., Ciliary Neurotrophic Factor Protects Retinal Ganglion Cells from Secondary Cell Death During Acute Autoimmune Optic Neuritis in Rats, Brain Pathol. Oct. 2004, 14(4):378-87.
Meer-Franke et al., Characterization of the Signaling Interactions That Promote the Survival and Growth of Developing Retinal Ganglion Cells in Culture, Neuron 15, 805-19. 1995.
Mu et al., Discrete gene sets depend on POU domain transcription factor Bm3b/Bm-3.2/POU4f2 for their expression in the mouse embryonic, Devel. 131. 1197-1210. 2004.
Shen et al., Retinal Ganglion Cells Lose Trophic Responsiveness after Axotomy, Neuron 23, 285-95, 1999.
Yoles et al., Degeneration of Spared Axons Following Partial White Matter Lesion: Implications for Optic Nerve Neuropathies, Exp Neurol. 153, 1-7, 1998.

\* cited by examiner

METHODS OF IDENTIFYING NEUROPROTECTIVE COMPOUNDS FOR RETINAL GANGLION CELLS

This application is a National Stage application of PCT application PCT/US2006/015457 filed on Apr. 24, 2006, which was published in English under PCT Article 21(2) on Nov. 2, 2006, and which claims the benefit of provisional application Ser. No. 60/674,202 filed Apr. 22, 2005. These applications are incorporated herein by reference in their entireties.

This application claims the benefit of and incorporates by reference provisional application Ser. No. 60/674,202 filed Apr. 22, 2005.

FIELD OF THE INVENTION

The invention relates to neuroprotective compounds and their use to treat optic neuropathies.

BACKGROUND OF THE INVENTION

The initial insult for many retinal ganglion cell (RGC) diseases, including glaucoma, optic neuritis, anterior ischemic optic neuropathy, traumatic optic neuropathy, and compressive optic neuropathy, is at the axon level. There is a need in the art for neuroprotective molecules which can support RGC survival and regeneration (e.g., neurite outgrowth).

DETAILED DESCRIPTION OF THE INVENTION

Embodiments of the invention include neuroprotective compounds, methods of using the compounds to treat optic neuropathies, and screening methods for identifying additional neuroprotective compounds.

Compounds of the Invention

Compounds of the invention are useful for preserving or restoring vision in patients with blinding optic nerve diseases such as glaucoma, optic nerve stroke, anterior ischemic optic neuropathy, traumatic optic neuropathy, optic neuritis, injury to the optic nerve from elevated intracranial pressure, and compression of the optic nerve by brain tumors.

Definitions

"$C_1$-$C_6$ alkyl" is a monovalent linear or branched saturated hydrocarbon radical with 1, 2, 3, 4, 5, or 6 carbons. A $C_1$-$C_6$ alkyl can be optionally substituted with one or more of oxygen, nitrogen, halogen, and sulfur. A $C_1$-$C_6$ alkyl also can be optionally interrupted with one of more nitrogen or oxygen atoms. Examples of $C_1$-$C_6$ alkyl are methyl, ethyl, propyl, isopropyl, sec-butyl, tert-butyl, n-butyl, n-pentyl, sec-pentyl, tert-pentyl, n-hexyl, isopentyl, fluoromethyl, trifluoromethyl, hydroxybutyl, dimethylcarboxyalkyl, aminoalkyl, and benzylpropyl.

"$C_1$-$C_6$ alkenyl" is a monovalent linear or branched hydrocarbon radical with 1, 2, 3, 4, 5, or 6 carbon atoms which has one or more double bonds. A $C_1$-$C_6$ alkenyl can be optionally substituted with one or more of oxygen, nitrogen, halogen, and sulfur. A $C_1$-$C_6$ alkenyl also can be optionally interrupted with one or more nitrogen or oxygen atoms. Examples of $C_1$-$C_6$ alkenyl are vinyl, allyl and dimethylallyl.

"$C_1$-$C_6$ alkoxy" is the radical —OR', wherein R' is an optionally substituted $C_1$-$C_6$ allyl. Examples of alkoxy include methoxy, ethoxy, propoxy, 2-propoxy, butoxy, sec-butoxy, tert-butoxy, pentyloxy, hexyloxy, fluoromethoxy, and iodoethoxy.

"Halogen" includes sodium, fluorine, chlorine, and bromine.

Structural Formulae

Some compounds of the invention have structural formula (I):

wherein:
X and Y are independently NH, S or O; and
R is selected from the group consisting of:
NR$^1$R$^2$, wherein R$^1$ and R$^2$ are independently hydrogen or linear or branched C$_1$-C$_6$ alkyl;
linear or branched C$_1$-C$_6$ alkyl; and
phenyl, unsubstituted or substituted with one or more of O, S, OR$^1$, NH$_2$, halogen, and C$_1$-C$_6$ alkyl.

Particular compounds of structural formula (I) include:

Other compounds have structural formula (II):

wherein:
R and R$^1$ are either
(1) independently selected from the group consisting of:
hydrogen, C$_1$-C$_6$ alkenyl optionally substituted with one or more of =O, =S, OR, and NH$_2$;
phenyl, unsubstituted or substituted with one or more of =O, hydroxy, or C$_1$-C$_6$ alkyloxy; or
(2) when taken together with the nitrogen to which they are attached, form a heterocycle selected from the group consisting of piperazinyl, piperidinyl, pyrrolidinyl, and morpholinyl;
R$^2$ and R$^3$ are independently selected from the group consisting of hydrogen; C$_1$-C$_6$ alkyl; NR$^5$R$^6$; phenyl optionally substituted with one or more of =O, C$_1$-C$_6$ alkyloxy, hydroxy, and benzylidine hydrazine optionally substituted with one or more hydroxyl groups;
R$^4$ is hydrogen or nitro; and
R$^5$ and R$^6$ are hydrogen or, when taken together with the nitrogen to which they are attached, form a heterocycle selected from the group consisting of piperazinyl, piperidinyl, pyrrolidinyl, and morpholinyl,
with the proviso that R and R$^1$ cannot both be hydrogen.

Compounds of structural formula (II) include:

4-amino-4-[(4,6-dimethyl-2-pyrmidinyl)amino]-3-buten-2-one

N$^2$,N$^4$-Bis-(3-methoxy-phenyl)-6-methyl-5-nitro-pyrimidine-2,4-diamine

4-[(2,6-Di-morpholin-4-yl-pyrimidin-4-yl)-hydrazonomethyl]-benzene-1,3-diol

N-(2,6-Di-morpholin-4-yl-pyrimidin-4-yl)-N'-(3-nitro-benzylidene)-hydrazine

Other compounds have structural formula (III):

(III)

wherein:

can be a five-membered ring optionally substituted with =O;
n and m are independently=0 or 1;
p is 0, 1, 2, 3, or 4;
$R^1$, $R^2$, and $R^3$ are independently selected from the group consisting of $C_1$-$C_6$ alkyl, $C_1$-$C_6$ alkoxy, hydroxy, halogen, amino, and aminosulfonyl optionally substituted with phenyl, wherein the phenyl is optionally substituted with one or more halogen atoms;
X is —C(O)NHN=CH($CH_2$)$_p$—, —($CH_2$)$_p$C(O)OR', —NHN=CH($CH_2$)$_p$—, —NHCH=R'—, piperazinyl, piperidinyl, and pyrrolidinyl;
R' is $C_1$-$C_6$ alkyl; and
$R^4$ is selected from the group consisting of phenyl, optionally substituted with one or more of hydroxyl, $C_1$-$C_6$ alkoxy, hydroxycarbonyl, and halogen; $C_1$-$C_6$ alkyl, optionally substituted with phenyl; and thiophenyl.

Compounds of structural formula (III) include:

N-[4-(2,4-Difluoro-phenylsulfamoyl)-phenyl]-acetamide o-Tolylamino-acetic acid
[1-(4-bromo-phenyl)-ethylidene]-hydrazide 2-[N'-(4-Hydroxy-3-methoxy-benzylidene)-hydrazino]-N-(4-methoxy-phenyl)-2-oxo-acetamide

7

N-(4-Bromo-phenyl)-2-oxo-2-(N'-thiophen-2-ylm-ethylene-hydrazino)-acetamide p-Tolylamino-acetic acid
(5-bromo-2-hydroxy-benzylidene)-hydrazide

2-[N'-(2,3-Dimethoxy-benzylidene)-hydrazino]-N-(2-methoxy-phenyl)-2-oxo-acetamide methyl 4-[(4-ethyoxyphenyl)amino]-4-oxobutanoate

8

3-(4-Benzhydryl-piperazin-1-yl)-1-(3-methoxy-phenyl)-pyrrolidine-2,5-dione

4-{3-[(4-Chloro-phenylcarbamoyl)-methylsulfanyl]-2,5-dioxo-pyrrolidin-1-yl}-benzoic acid Other compounds have the following structural formulae:

4-(hydroxyamino)-N,N,3,7,7-pentamethylbicyclo[4.1.0]heptan-3-aminium chloride; or 4-(e-chloro-4-hydroxy-5-methoxyphenyl)-6-methyl-2-oxo-1,2,3,4-tetrahydro-5-pyrimidine carboxylate Compounds of the invention can be made using standard organic chemical techniques. Starting materials are known compounds and can be obtained commercially or by standard procedures of organic chemistry. Alternatively, compounds can be obtained from the DIVERSET™ library (Chembridge).

In some embodiments, compositions comprising compounds of the invention do not contain DMSO. Compounds of the invention are isolated, i.e., they are not members of a chemical library or in a 96-well plate. Preferably, compounds of the invention are present in an "ophthalmically acceptable formulation," as defined below.

Therapeutic Methods

Compounds of the invention can be used as active agents to treat a variety of clinical and experimental optic neuropathies. These neuropathies include glaucoma, optic nerve stroke, optic neuritis, anterior ischemic optic neuropathy, traumatic optic neuropathy, compressive optic neuropathy (e.g., compression due to elevated intracranial pressure or brain tumors), and hereditary neuropathies, such as Leber's hereditary optic neuropathy. "Patient" as used herein includes both humans and animals (e.g., rats, mice, sheep, pigs, dogs, cats, and non-human primates).

Pharmaceutical Preparations and Routes of Administration

Compounds of the invention can be formulated as pharmaceuticals using methods well known in the art. Formulations can be for direct delivery to the eye or for systemic administration. In preferred embodiments, compounds of the invention are present in an "ophthalmically acceptable formulation," which is a formulation which is specifically suitable for administration to the eye. Ophthalmically acceptable formulations include, for example, topical ocular drops, gels, and ointments. Ophthalmically acceptable formulations can be present in eye droppers or in slow-release devices in the cul-de-sac or implanted adjacent to the sclera or within the eye. In some embodiments ophthalmically acceptable formulations are administered by periocular, conjunctival, sub-Tenons, intracameral, or intravitreal injection. Peribulbar and retrobulbar administration also is contemplated.

Systemic routes include oral, intravenous, rectal, vaginal, transmucosal, intestinal, parenteral (including intramuscular, subcutaneous, intramedullary routes), intranodal, intrathecal, direct intraventricular, intravenous, intraperitoneal, intranasal, transdermal, and topical routes.

Pharmaceutical compositions comprise one or more compounds of the invention either in aqueous solution or suspension, and can contain one or more preservatives for multidose use and other conventionally employed components (e.g., buffers, antioxidants, etc). For example, aqueous eye drops, gels and ointments can be formulated according to conventional technology and typically include one or more excipients. Topically administrable compositions may contain tonicity-adjusting agents, such as mannitol, glycerin, potassium chloride, or sodium chloride; preservatives such as chlorobutanol, thimerosal, phenylmercuric acetate, phenylmercuric nitrate, benzalkonium potassium, benzalkonium chloride, polyquaternium-1, or chlorhexidine; buffering agents, such as phosphates, borates, carbonates and citrates; and thickening agents, such as high molecular weight polymers, such as hydroxyethylcellulose, hydroxypropylcellulose, poloxamers, carboxymethylcellulose, and polyvinyl alcohol.

Various buffers and means for adjusting pH can be used so long as the resulting preparation is pharmacologically acceptable, preferably ophthalmically acceptable. Accordingly, buffers include but are not limited to, acetate buffers, citrate buffers, phosphate buffers, and borate buffers. Acids or bases may be used to adjust the pH of these formulations as needed. Ophthalmically acceptable antioxidants include, but are not limited to, sodium metabisulfite, sodium thiosulfate, acetylcysteine, butylated hydroxyanisole, and butylated hydroxytoluene.

The compounds can be used as an adjunct to ophthalmic surgery, such as by vitreal or subconjunctival injection following ophthalmic surgery. The compounds can be used for acute treatment of temporary conditions, or can be administered chronically, especially in the case of degenerative disease. The compounds may also be used prophylactically, especially prior to ocular surgery or noninvasive ophthalmic procedures, or various types of neurosurgery.

Dosage

A "therapeutically effective amount" (also called a "therapeutically effective dose") is the amount of an active agent which, when administered to a patient, results in a measurable improvement in a symptom of the disease being treated (e.g., an improved laboratory value such as erythrocyte sedimentation rate; improved visual acuity; restoration of a portion of the visual field; improved brightness perception; improved color vision; improved contrast sensitivity).

Determination of therapeutically effective amounts is well within the capability of those skilled in the art. Data obtained from cell culture assays as disclosed herein and/or from studies with animal models can be used to determine initial human doses. Appropriate animal models for the relevant diseases are known in the art. See, e.g., Bernstein et al., *Mol. Vision*. 2006; 12:147-155 (optic nerve stroke); Bernstein et al., Invest Opthalmol Vis Sci 2003; 44:4153-62, and US 2004/0228795 (anterior ischemic optic neuropathy); Goldenberg-Cohen et al., Invest Opthalmol Vis Sci 2005; 46:2716-25 (ischemic optic neuropathy); Ko et al., Free Radic Biol Med. 2005 Aug. 1; 39(3):365-73 (glaucoma); Maier et al., Brain Pathol. 2004 October; 14(4):378-87 (autoimmune optic neuritis); Guy & Hauswirth, Proc Natl Acad Sci USA. 1998 Nov. 10; 95(23):13847-52 (optic neuritis); and Yoles et al., *Exp Neurol*. 153, 1-7, 1998 (optic nerve crush).

Usual patient dosages for systemic administration range from 0.001 mg/kg per day to 1000 mg/kg per day. The amount of composition administered will, of course, be dependent on the subject being treated, on the subject's weight, the severity of the neuropathy, the manner of administration and the judgment of the prescribing physician.

Screening Assays

Screening assays of the invention identify neuroprotective compounds. A "neuroprotective compound" is a compound which supports substantially the same number of outgrowth neurons (as defined above) as BDNF and forskolin. Screening assays of the invention combine a sensitive bioassay with a high throughput screen. One specific embodiment of a screening assay is described in Examples 2 and 3, below. Generally, screening assays of the invention involve plating retinal ganglion cells into 96-well plates, exposing them to test compounds (e.g., at a concentration of 30 µM), and visualizing the cells to determine viability, extent of neurite outgrowth (number of neurites per cell, length, number and length of branch points, etc.). See Example 3.

Retinal Ganglion Cell Culture System

The retina contains a mixed population of cells which can be significantly enriched for RGCs using an efficient two-step immunomagnetic purification. RGCs obtained by this method have morphologies typical of RGCs in cell culture. For example, after five days in culture the cells develop a robust arbor of neurites typical of what has been reported for RGCs (FIG. 1; Example 1). Addition to the basic culture medium of factors known to promote RGC survival (e.g., BDNF and forskolin) increases overall cell survival, particularly survival of neurite-bearing cells.

Methods of isolating RGCs are known in the art and any such methods can be used. See, e.g., Barres et al., *Neuron* 1, 791-803, 1988. Primary retinal cell cultures are most successful when obtained from immature animals. Rats, because of their size, provide useful quantities of cells in comparison with other rodents. Thus, early postnatal rat retinas are particularly useful, but other retinas (e.g., mouse, rat, cat, monkey) also can be used.

Immunomagnetic Enrichment of Retinal Ganglion Cells

In a preferred embodiment, retinas are dissected from postnatal day 3 to 5 Sprague Dawley rats, digested with activated papain (Worthington) and DNase (Sigma) and dissociated by trituration. The average total number of cells obtained from a postnatal rat retina of this age is 10-15 million. The number of ganglion cells in a rat retina is about 40,000 (approximately 80% of retinal ganglion cells are labeled by retrograde transport). Thus, retinal ganglion cells are less than 1 percent (0.2% of cells) of the cells in a mixed culture. In a typical experiment, seeding 1500 retinal ganglion cells per well of a 96-well plate requires introducing an estimate of 750,000 cells into each well (200 µl of $4 \times 10^6$ cells/ml).

Methods of purifying RGCs are known. See, e.g., Barres et al., Neuron 1, 791-803, 1988. In a preferred method, immunomagnetic depletion of macrophages is performed by incubating the retinal cell suspension with magnetic microbeads (Dynal Biotech) conjugated to mouse anti-rat cd11 b/c antibody (BD Biosciences, Pharmingen) and removal of the beads by magnetic separation. This is followed by immunomagnetic selection of Thy1 antigen bearing RGCs by incubating the cell suspension with magnetic microbeads conjugated to mouse anti-rat Thy1 antibodies (Chemicon) and selection by magnetic separation. In a final step, the magnetic beads are cleaved from the cells by incubation in DNAse which cuts the DNA linker between the magnetic bead and the antibody. See Example 2.

Culture Conditions

Methods of maintaining retinal ganglion cells in culture are well known and any such methods can be used. Cells preferably are grown on poly-d-lysine/laminin coated plastic plates in a basic medium consisting of Neurobasal media, B27 supplement, glutamine, and penicillin/streptomycin. See Example 2. A seeding density of 4,000 cells per well is preferred because it maintains a density low enough to permit the effect (e.g., neurite outgrowth) of test compounds and positive controls to be observed.

Exposure to Test Compounds

Test compounds which can be screened can be pharmacologic agents already known in the art or can be compounds previously unknown to have any pharmacological activity. The compounds can be naturally occurring or designed in the laboratory. They can be isolated from microorganisms, animals, or plants, and can be produced recombinantly, or synthesized by chemical methods known in the art. Combinatorial chemical libraries are particularly useful sources of test compounds. Many such libraries are commercially available, for example, from Chembridge (e.g., DIVERSET™, a diversity-oriented compound library). Other libraries include non-small molecule libraries such as the lentivirus-based RNA interference (RNAi) library (Viral shRNA Library Consortium; http://filetype web.wi.mit.edu/sabatini/pub/siRNA_consortium.html) and cDNA expression libraries, particularly retinal expression libraries (e.g., Leveillard et al., Nature Genetics 36, 755-59, 2004).

DIVERSET™ Compound Library

The DIVERSET™ library (Chembridge Inc, San Diego, Calif.) is a diversity-oriented library of synthetic small molecules from the Chembridge collection of 300,000 chemicals. The organizing criteria for the collection are diversity, heterocycle-containing, predicted bioactivity, low molecular weight, production via multi-step large-scale manual synthesis, and over 95% purity. The entire DIVERSET™ collection consists five groups of 10,000 compounds dissolved in DMSO.

Compounds in the library are in a concentration of 3 mM in DMSO and are individually arrayed in wells of a 96 well plate. Negative controls can be placed in column 1 and 12, wells A through E. Positive controls can be placed in column 1 and 12, wells F through H. The plates can be stored at −20° C. Preferably one compound is tested per well. If desired, initial screens can be carried out with several compounds per well. Obviously, the location of test compounds and controls in any particular plate is arbitrary and can be varied as desired.

The concentration of the test compounds can be varied depending, for example, on the nature of the test compound. Peptide trophic factors generally demonstrate their maximal effect on RGCs in a range of 0.1 ng/ml (e.g., CNTF) to 10 ng/ml (e.g., BDNF) (Meer-Franke et al., Neuron 15, 805-19, 1995). The small molecule forskolin demonstrates a maximal effect on RGCs at 3 µM (Shen et al., Neuron 23, 285-95, 1999). Lithium is effective at 1 mM (Huang et al., Invest. Opthalmol. Vis. Sci. 44, 347-54, 2003). Concentration ranges can be tested or an initial test can be done with only one concentration. A screening concentration of 20 to 30 µM is useful for small molecules such as those in the DIVERSET™ library.

The preferred solvent for test compounds is water. DMSO, a well known biologic solvent, is a useful vehicle for compounds which either are not soluble in water or which degrade rapidly in the presence of moisture. One percent DMSO has no apparent toxicity in the screening assay of the invention; concentrations greater than 1% can cause toxicity.

Cells can be exposed to test compounds for various times. Typical exposure times include 10, 20, 30, 45, 60, 90, and 120 minutes. Cells can be monitored during the exposure period, and the times can be varied as desired.

Positive and negative controls are preferably included. Compounds known to increase RGC survival and/or promote neurite outgrowth can be used as positive controls. Such compounds include forskolin and BDNF. Vehicle (e.g., DMSO) or medium can be used as negative controls.

Imaging of Cells

After exposure to test compounds as described above, cells in the culture are visualized to determine the effect of the test compounds on various parameters such as cell viability, morphology, neurite outgrowth, neurite branching, number of branch points, length of neurite branches, mean neurite length per neuron, and neurite count per neuron. In a typical experiment, the number of outgrowth neurons is determined. "Outgrowth neurons" are cells with neurites which exceed a threshold of one standard deviation with respect to total neurite length and neurite count based on the same measurements for cells grown in reference wells without growth factors.

Viability can be assessed as is known in the art using nuclear stains, such as Hoechst dye (e.g., bisbenzimide H 33342); 4',6-diamidino-2-phenylindole (DAPI); Pyronin Y; or acridine orange. Various stains and dyes can be used to visualize living cells and their neurites. These include, for example, hydrophilic dyes which are trapped in the cytoplasm and hydrophobic dyes which are carried in organdies or in cell membranes. Suitable examples include, but are not limited to, calcein acetoxymethyl (AM), calcein blue AM, and calcein red-orange AM (Molecular Probes).

Validation of Neuroprotective Compounds

Validation of neuroprotective compounds typically is done by demonstrating a dose response relationship. Although the developed technique for performing cell culture is effective and objective, it is desirable to assess the outcome of a screen using a different technique. Thus, for example, the technique of culturing cells on poly d-lysine and laminin coated coverslips in 24 well culture dishes under various culture conditions can be followed by immunostaining with anti-neurofilament antibody and quantitative analysis.

Retinal ganglion cell harvest and immunopurification are performed as described above and in the specific Examples, below. A concentration range of neuroprotective compounds to be validated is prepared and added to test wells (e.g., to achieve final concentrations of 3 μM, 10 μM, 15 μM, 30 μM, 60 μM, 90 μM, 120 μM, and 150 μM in 1% DMSO in each well). For a neuroprotective compound obtained from the DIVERSET™ library, for example, 1 mg of desiccated compound can be resuspended in 22.2 μl of DMSO to a final stock solution of 150 mM. If the compound does not go into solution, the stock is further diluted until it is in solution. Afterwards, the solution can be stored in the dark at −20° C.

Neuroprotective compounds and positive control factors are added to the appropriate wells of a 96-well plate (e.g., 25 μl to each well in a 5× concentration prior to the seeding cells in a volume of 100 μl giving a final volume of 125 μl). Cells are incubated, stained, and imaged as described above and in the specific Examples, below. Experiments preferably are performed in duplicate. Following normalization to a negative control (e.g., a well containing medium only), a dose response curve can be plotted. Statistical software (e.g., from SPSS) can be used to perform curve fitting and analysis.

After determination of the dose response relationship and concentration at which the neuroprotective compound has it is maximal effect in culture, cells can be cultured on poly d-lysine and laminin coated cover slips (BD Pharmingen) in the presence of the neuroprotective compound, with appropriate positive and negative controls. After 120 hours in culture, the cells can be fixed and stained to visualize neurites.

For example, in one embodiment cells are fixed with 4% paraformaldehyde, washed with PBS, blocked with PBS/ 0.1% Triton X/20% goat serum, and incubated overnight in PBS/0.1% Triton X/20% goat serum containing 1:100 dilution of rabbit anti-neurofilament (68 kd) antibody (Chemicon). After rinsing, the cells are incubated for one hour in 1:500 dilution of goat anti-rabbit IgG Alexa 594 (red) (Molecular Probes), rinsed and counterstained with 5 μM Hoechst. Coverslips are mounted in aqueous mounting medium on glass slides. Twenty randomly selected cells are imaged using a Zeiss fluorescent/DIC microscope. The number of cells with neurite outgrowth at 3 different radii is determined (Scholl analysis) and compared using Student t test.

All patents, patent applications, and references cited in this disclosure are expressly incorporated herein by reference. The above disclosure generally describes the present invention. A more complete understanding can be obtained by reference to the following specific examples, which are provided for purposes of illustration only and are not intended to limit the scope of the invention.

Example 1

Retrograde Labeling of Retinal Ganglion Cells In Vivo

Neonatal animals are anesthetized by cooling them in ice, with a barrier to prevent direct contact of the rat with the ice. The rats are placed in a stereotaxic device to secure the head. The procedure is performed using a sterile drape, gloves, and instruments. The skin is prepped with topical Betadine. The skull surface is exposed by sharp dissection through the skin and subcutaneous tissue. After exposing the skull surface and identifying the bregma, the locations of four injections targeting the superior colliculus are defined using coordinates from the stereotaxic atlas *The Rat Brain* by Paxinos and Watson.

A craniotomy is performed above the right and/or left hemisphere. The dye [Fluoro-gold dye 4% solution in saline (Fluorochrome Inc)] is injected using a glass microcannula attached to a 5 μl Hamilton syringe via polyethylene tubing at a rate of 1 μl/minute. One microliter is injected at each of the four points centered over the superior colliculus. The surgery is completed in about 30 minutes and usually requires one repeat injection. Animals are monitored during the procedure for respiration, coloration, and response to paw stimulation. The procedure is discontinued if the animals develop distress. Following completion of the procedure, the skin over the wound is stapled. Animals are allowed to recover and are placed with their nursing mother. Animals are monitored daily prior to euthanasia for signs of wound infection, respiratory distress, coloration, poor nursing, and the presence of a milk spot.

Example 2

Purified Retinal Ganglion Cell Culture System

An efficient two-step immunomagnetic purification of a mixed cell population obtained from postnatal rat retina is used to provide a highly enriched population of RGCs for culture. The first step is an immunomagnetic depletion of Thy1-bearing non-RCGS using a cd11b/c. The second step is an immunomagnetic selection of RGCs with an antibody that binds Thy1 on the RGC cell surface. The cells are then released from the magnetic beads by digesting the DNA linker with a low concentration of DNase. Cells are grown on poly-d-lysine/laminin coated plastic plates in a basic medium (Neurobasal media, B27 supplement, glutamine, and penicillin/streptomycin). These cultures are highly enriched for RGCs. The RGCs are morphologically typical of RGCs in cell culture and reproducibly respond to BDNF and forskolin as expected for RGCs.

To assess the efficiency of our selection technique, RGCs were retrogradely labeled by bilateral transcranial injection of DiI into the superior colliculus three days prior to sacrifice, as described in Example 1. With this technique, 94.8±1.3 percent of the cells in culture were labeled.

Figure 1:
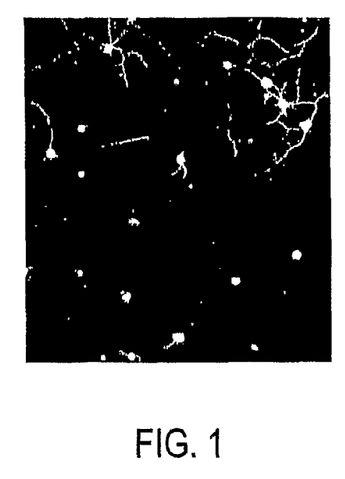
FIG. 1. RGCs after 5 days in culture in the presence of BDNF and forskolin. The cells demonstrate robust neurite outgrowth typical of RGCs.

After five days in culture, the cells have developed a robust arbor of neurites typical of what has been reported for RGCs (FIG. 1). Finally, the addition of factors known to promote RGC survival (e.g. BDNF and forskolin) to the basic culture medium results in increased overall cell survival and, more significantly, in the survival of neurite-bearing cells.

Between 18 and 20 retinas typically can be harvested in a procedure which takes less than 5 hours. Based on an estimate of 100,000 RGCs per retina, the procedure's yield is approximately 50%. Thus, we typically harvest 1 million cells per experiment. Initial post-seeding viability is typically estimated by staining with Hoechst (a blue fluorescent nuclear dye taken up by all cells) and TOTO3 (a far red fluorescent nuclear dye retained by dead cells). Viability ranges from 90 to 95% using this technique.

The purified Thy-1 immunoreactive cells are resuspended in growth media (Neurobasal media, B27 supplement, 2 mM glutamine, and 1 U/ml penicillin/streptomycin) and quantified using a hematocytometer. Cells are seeded in 100 μl at a density of 4000 cells/well (150/mm$^2$) in 96 well culture dishes (Falcon) that had been sequentially coated with poly-d-lysine (0.01 mg/ml) and laminin (0.01 μg/μl) (Sigma). Each well either contains 25 μl of media alone or 5× drug or 5×BDNF and forskolin. Final concentrations are: DMSO (1%), drug (20 to 30 μM), BDNF (50 ng/ml) and forskolin (10 μM). Culture dishes are placed in an incubator maintained at 37° C. and 5% $CO_2$. One hour after seeding, a post-seeding viability is determined by staining with Hoechst and TOTO3 and calculating the percent of live cells.

Example 3

High Throughput Analysis

Given a yield of approximately 1 million cells with a relatively high viability, a seeding density of 4000 cells per well is enough to fill two 96 well plates, which makes this culture system robust enough to achieve a high throughput. Analysis of a variety of outcomes as discussed below is performed after 120 hours. With optimization of our efficiency and maximum use of resources, one can prepare and analyze between 6 and 8 ninety-six well plates per week.

Staining

After 120 hours of incubation, cells are stained with 5 μM Hoechst and 10 μM Calcein AM (Molecular Probes). Calcein AM (Calcein acetoxymethyl), the dye that is used to stain living cells and their neurites, is a green dye that is permeant to living cells. After internalization by cells, the nonfluorescent calcein AM is converted to fluorescent calcein upon hydrolysis of the acetoymethyl ester by intracellular esterases. Cleavage of the AM group occurs spontaneously when calcein AM is suspended in aqueous solution resulting in a significant increase in background fluorescence over time. TOTO3, which stains the nuclei of dead cells, can be used to determine viability.

Imaging

Fifteen stereotypic field are autofocus imaged on a Cellomics KINETICSCAN® High Content Scan Reader using epifluorescence and filter sets corresponding to each of the two dyes. This instrument employs a Zeiss fluorescence microscope, a temperature and $CO_2$ live cell chamber, an integrated liquid handling system, and image analysis software that permits staining, imaging, and analysis of the cells and their neurites in approximately 5 hours per plate. Scanning the entire plate takes just over three hours and collects 2880 images.

Image Analysis

Images are processed using the Cellomics Extended Neurite Outgrowth software program. In the initial image processing, cells are identified on the Hoechst channel and selected based on size such that of clusters of cells may be excluded from analysis. In addition, each nuclei on the Hoechst channel is matched to a calcein-stained cell and counted as a "valid neuron" (i.e., a live cell). Neurons can be further selected based on size in the calcein channel. The Extended Neurite Outgrowth program is used to trace neurites extending from these selected neurons. The mean neurite length, mean neurite count, mean number of branch points, and mean number of crosspoints are determined. In addition, the percent of cells with neurite features (e.g., neurite length, neurite count) surpassing a threshold of one standard deviation above the mean neurite characteristic of a set of reference wells containing cells and growth medium without additional growth factors is determined. The "neurite outgrowth" measurement is based on the combined mean neurite length and mean neurite count. Cells surpassing a threshold of one standard deviation above the mean neurite outgrowth index for control wells are regarded as "outgrowth neurons." Thus far, the number of outgrowth neurons is the most reliable indicator of the presence of growth factors in our system and is the primary endpoint of this assay.

Statistical Analysis

The outgrowth count for each well is normalized to counts from all wells except for positive controls. Studies are done in quadruplicate, and a mean and standard deviation is calculated for each compound and a z statistic as an indicator or reproducibility calculated:

$$z = 1 - \frac{(3 \times \text{standard deviation of controls}) + (3 \times \text{standard deviation of drug})}{|(\text{mean of drug}) - (\text{mean of controls})|}$$

Example 4

Culture System Demonstrates that Bone Morphogenic Proteins Promote RGC Survival

Bone morphogenetic proteins (BMPs), originally discovered for their capacity to promote osteogenesis, are members of the TGFβ superfamily and are known to regulate a variety of cell functions in multiple tissues including proliferation, apoptosis, differentiation, and morphogenesis (Hogan, *Genes Dev.* 10, 1580-94, 1996; Reddi, *Nat. Biotechnol.* 16, 247-52, 1998). TGFβ and BMP signaling has been implicated in retinal neurogenesis and axonal pathfinding (Anchan & Reh, *J. Neurobiol.* 28, 133-45, 1995; Liu et al., *Devel. Biol.* 256, 34-48, 2003). Microarray and quantitative reverse transcription-PCR (RT-PCR) analyses of gene expression in Brn3b knockout mice, which have a 70% reduction in the number of retinal ganglion cells, showed a 12-fold reduction in expression of the BMP-related myostatin/Gdf8 (Growth and differentiation factor 8) (Mu et al., *Devel.* 131, 1197-1210, 2004). Based on the accumulated data suggesting a role for BMPs in retinal neuronal development and pathfinding, we examined the effects of BMPs on the behavior of cultured RGCs.

Figure 2:
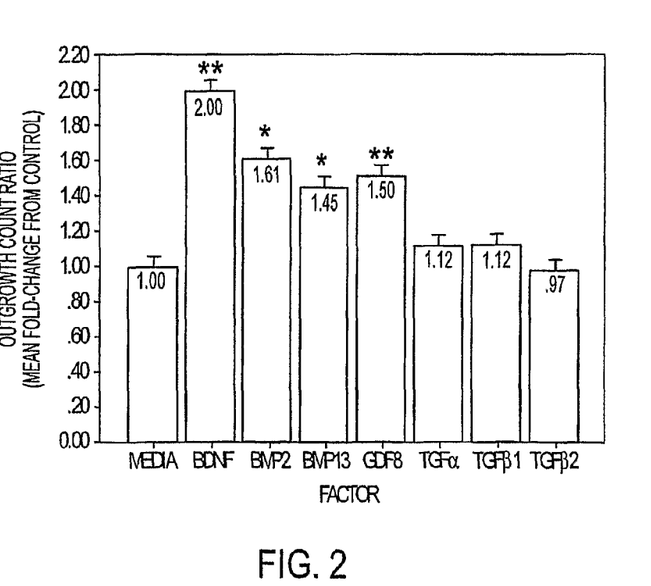
FIG. 2. Bar graph demonstrating that bone morphogenic proteins (BMPs) promote survival of "outgrowth neurons." "Outgrowth neurons" are cells with neurites which exceed a threshold of one standard deviation with respect to total neurite length and neurite count compared to the same measurements for cells grown in reference wells without growth factors. The "outgrowth count ratio" (X-axis) is the mean fold-change from control. Statistically significant increases in the number of outgrowth neurons were observed in cultures treated with BDNF, BMP2, BMP13, and GDF8 (myostatin). For each independent experiment, the number of outgrowth neurons was normalized to the number of outgrowth neurons in cultures grown in medium only. * denotes $p<0.002$; ** denotes $p<0.0001$.

Based on the number of living cells present two hours after seeding, the 120 hour average survival without additional growth factors was 44.0±6.6%. The addition of BMP2, BMP13, TGFα, TGFβ1, or TGFβ2 (50 ng/ml) had no effect on overall cell survival. Addition of 50 ng/ml BDNF and GDF8 (myostatin) resulted in a slight increase in the number of surviving cells that did not reach statistical significance. However, the number of outgrowth neurons was significantly increased for BDNF, as well as all of the BMPs as a group (BMP2, BMP13, GDF8) (FIG. 2). The most robust effect was observed with BMP2 (outgrowth count ratio 1.61±0.80). No significant change in the number of outgrowth neurons was observed after addition of TGFα, TGFβ1, or TGFβ2.

Example 5

Primary Compound Screen

Figure 3:
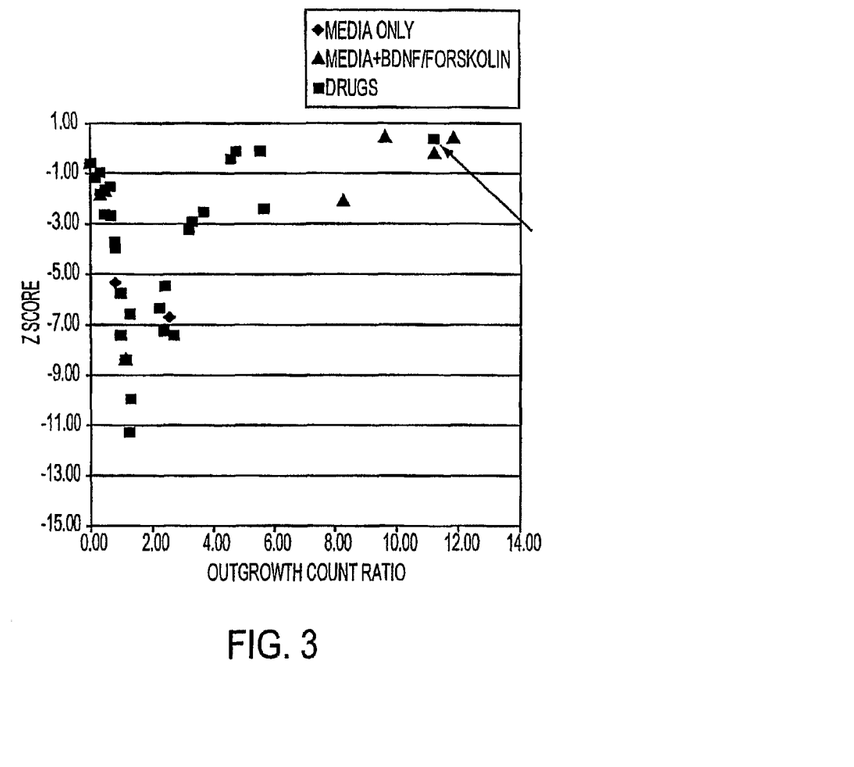
FIG. 3. Scatter plot of the normalized outgrowth ratio versus the z score for cells exposed to various compounds. Cells in the presence of BDNF and forskolin (triangles) show a high outgrowth ratio that is reproducible (high z score). The arrow indicates a neuroprotective compound that has an outgrowth and z score comparable to that of BDNF and forskolin.

To date we have evaluated over 1500 compounds from the Chembridge DIVERSET™ library. Eighteen compound plates were analyzed. Each compound plate has an array of 80 compounds and was evaluated in quadruplicate. Identified neuroprotective compounds were validated and selected for further analysis based upon the size and reproducibility of the response. The size of the response was compared across plates after the number of neurons with neurite outgrowth was normalized to the response of the entire plate except for the positive controls. The reproducibility of the response was determined by calculating a z statistic which accounts for the variation in response across plates (see Example 4). The normalized outgrowth ratio was plotted on the horizontal axis, and the z score was plotted on the y axis (FIG. 3). The screen identified 22 neuroprotective compounds.

Example 6

Validation by Dose-Response Analysis

Validation involves carrying out a dose response analysis over a range of dosages from 3 µM to 150 µM. Of the 22 neuroprotective compounds identified, five compounds were identified as promoting the survival of neurite bearing RGCs in culture in a dose-dependent manner.

Figure 4:
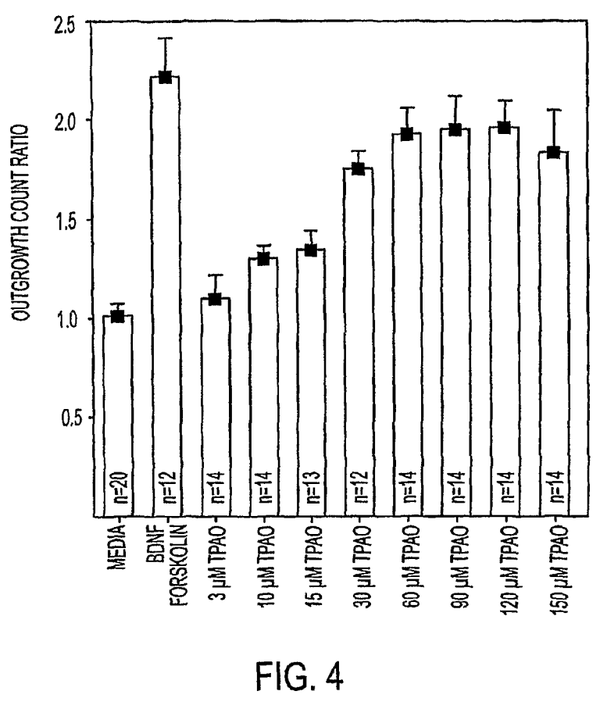
FIG. 4. Graph demonstrating that 2,2,6,6-tetramethyl-4-piperidinone O-acetyloxime (TPAO) promotes growth of RGCs in vitro in a dose-dependent manner. Immunopurified postnatal rat RGCs were cultured in increasing concentrations of TPAO in the presence of 1% DMSO. TPAO demonstrates RGC growth-promoting activity over a range of concentrations from 3 μM to 150 μM. The effect of TPAO was also demonstrated by culturing cells in 24-well plates on glass coverslips, immunostaining with a neurofilament antibody, and counting neurons with a neurite extension greater than one cell body in diameter. The effect of TPAO is synergistic with both BDNF and forskolin.
Figure 5A:
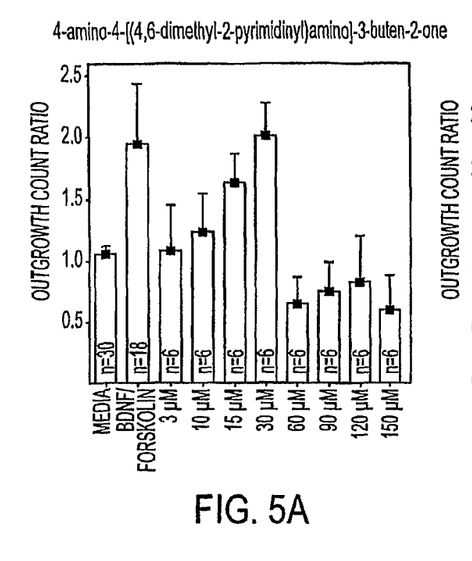
FIG. 5. Graphs demonstrating dose-dependent survival of neurite-bearing RGCs in the presence of each of four test compounds.
Figure 5B:
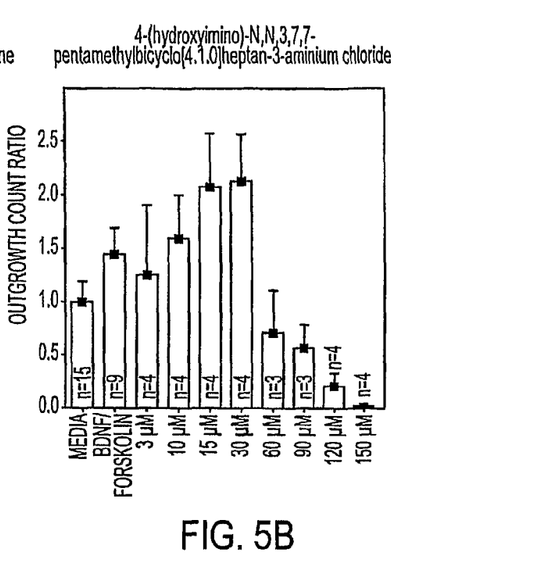
Figure 5C:
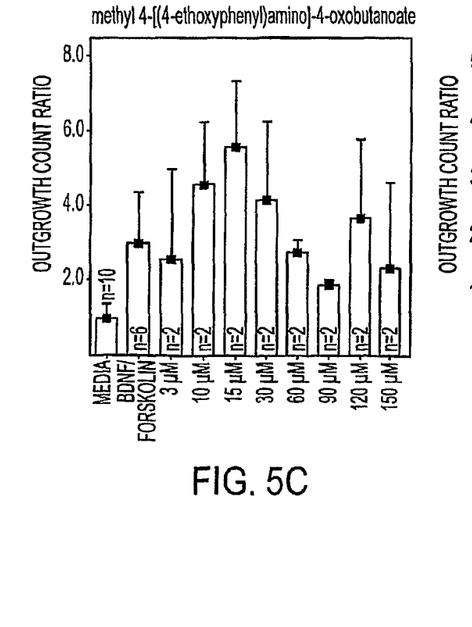
Figure 5D:
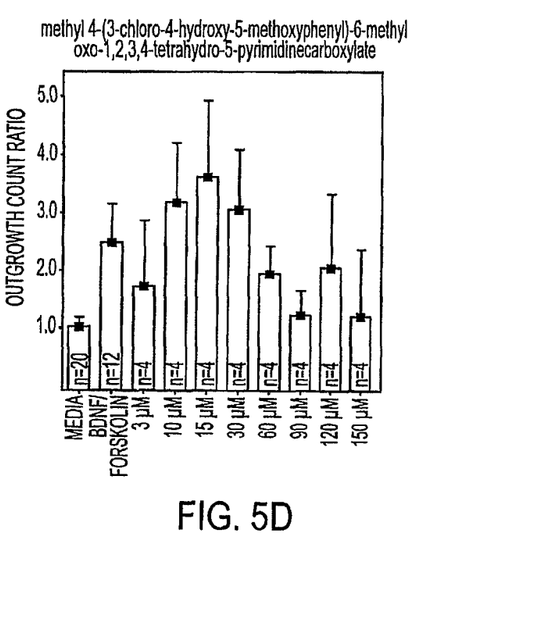

The most extensive analysis was performed with 2,2,6,6-tetramethyl-4-piperidinone O-acetyloxime (TPAO) (FIG. 4) which showed bioactivity in a range between 3 µM to 150 µM. The structure of TPAO is shown below:

Activity of TPAO was lost if the medium was changed at 24 hours, which demonstrates that the effect is reversible.

Four other compounds demonstrated RGC growth-promoting activity in doses ranging from 3 µM to 15-30 µM (FIG. 5). Higher concentrations of these compounds were associated with either reduced activity or toxicity. The compounds are shown below:

4-amino-4-[(4,6-dimethyl-2-pyrmidinyl)amino]-3-buten-2-one 4-(hydroxyamino)-N,N,3,7,7-pentamethylbicyclo[4.1.0]heptan-3-aminium chloride methyl 4-[(4-ethyoxyphenyl)amino]-4-oxobutanoate; and

4-(e-chloro-4-hydroxy-5-methoxyphenyl)-6-methyl-2-oxo-1,2,3,4-tetrahydro-5-pyrimidine carboxylate

Example 7

Identification of the Essential Bioactive Element

We extended our analysis of validated compounds to assess similar compounds in order to identify the essential bioactive element. A search of the library for compounds similar to 2,2,6,6-tetramethyl-4-piperidinone O-acetyloxime (TPAO) identified five compounds:

1) 2,2,6,6-tetramethyl-4-piperidinone O-(5H-dibenzo[b,f]azepin-5-ylcarbonyl)oxime hydrochloride

2) 2,2,6,6-tetramethyl-4-piperidinone O-(10,11-dihydro-5H-dibenzo[b,f]azepin-5-ylcarbonyl)oxime

3) 2,2,6,6-tetramethyl-4-piperidinone thiosemicarbazone

Figure 6:
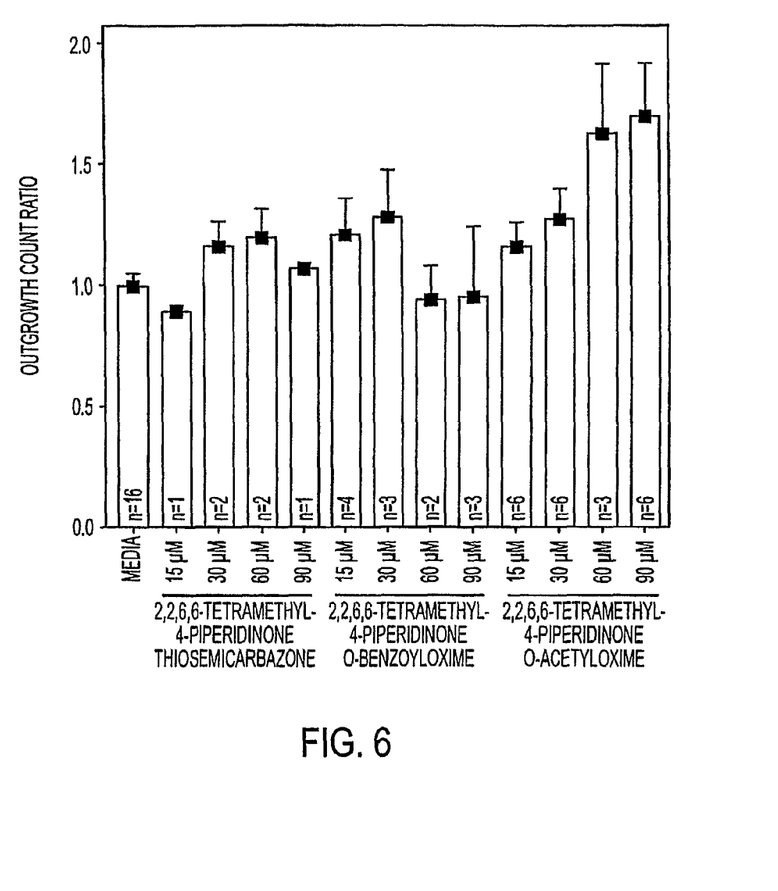
FIG. 6. Graph demonstrating dose-dependent activity of two compounds similar in structure to TPAO.

4) 2,2,6,6-tetramethyl-4-piperidinone O-benzoyloxime 5) 2,2,6,6-tetramethyl-4-piperidinone (2,4,6-trichlorophenyl)hydrazone oxalate Analysis of these five compounds at 4 different concentrations only showed activity for two of them (2,2,6,6-tetramethyl-4-piperidinone thiosemicarbazone and 2,2,6,6-tetramethyl-4-piperidinone O-benzoyloxime) (FIG. 6). In each case, the activity was less than that of TPAO but suggests that the element is necessary for activity of these particular compounds.

Example 8

Screening a Retinal cDNA Expression Library

Mixed populations of retinal cells and immunopurified populations of retinal ganglion cells are obtained from dissociated retinas of P6-P10 rats. Neonatal rats have experimental surgery, in which a retrograde fluorescent tracer is injected into the superior colliculus to label retinal ganglion cells prior to sacrifice. Following euthanasia, the retinas are dissected. The retinal cells are dissociated, and the cell population is enriched for RGCs as described in Example 2. The enriched cell population is seeded in 96-well plates in medium containing aliquots of the various molecules to be tested.

The molecules to be tested are derived from an expression library of mouse retinal cDNAs. Each cDNA in the library is in an expression construct under the control of a mammalian promoter. The expression constructed is transfected into COS cells, which express the encoded products (the molecules to be tested) into the medium. Positive control wells contain BDNF or CNTF. Negative control wells have no growth factors or supernatants added. Neuroprotective compounds are identified as described in Example 3.

The invention claimed is:

1. A high throughput method of identifying a neuroprotective compound, comprising:
   (1) contacting dissociated retinal cells with a magnetic bead coupled to an anti-cd11 b/c antibody:
   (2) separating cells bound to the anti-cd11 b/c antibody from other retinal cells to obtain a macrophage-depleted cell population;
   (3) contacting the macrophage-depleted cell population with a magnetic bead coupled to an anti-Thy1 antibody;
   (4) retaining cells bound to the anti-Thy1 antibody as a test enriched population of retinal ganglion cells;
   (5) culturing the test enriched population of retinal ganglion cells in the absence of growth factors;
   (6) contacting the test enriched population of retinal ganglion cells with a test compound previously unknown to have any neuroprotective pharmacological activity;
   (7) staining the test enriched population of retinal ganglion cells with at least a dye capable of staining living cells and their neurites and a dye capable of staining the nuclei of dead cells:
   (8) imaging retinal ganglion cells in the test enriched population to quantify the number of live cells and the extent of neurite outgrowth present in the test enriched population;
   (9) comparing the number of live cells and the extent of neurite outgrowth present in the test enriched population of ganglion cells contacted with the test compound to a control number of live cells and extent of neurite outgrowth present in a control enriched population of retinal ganglion cells cultured in the presence of BDNF and forskolin and the absence of the test compound; and
   (10) identifying the test compound as a neuroprotective compound if the number of live cells and/or the extent of neurite outgrowth in the compound treated population of retinal ganglion cells is statistically greater than the control number of live cells and/or extent of neurite outgrowth in the control enriched population of retinal ganglion cells grown in the presence of BDNF and forskolin and the absence of the test compound;
   wherein steps (1) to (10) are performed as a high throughput screen in a multi-well plate.

2. The method of claim 1 wherein test compound is a small molecule.

3. The method of claim 1 wherein the test compound is a cDNA expression product.

4. The method of claim 1 wherein the multi-well plate comprises a multi-well microtiter plate.

* * * * *

UNITED STATES PATENT AND TRADEMARK OFFICE
CERTIFICATE OF CORRECTION

PATENT NO. : 9,771,331 B2
APPLICATION NO. : 11/918987
DATED : September 26, 2017
INVENTOR(S) : John Barnwell Kerrison and Donald J. Zack Page 1 of 1

It is certified that error appears in the above-identified patent and that said Letters Patent is hereby corrected as shown below:

In Column 1, immediately after the title please insert the following paragraph (government support statement):
--STATEMENT OF GOVERNMENTAL INTEREST
This invention was made with government support under grant number EY013946, awarded by the National Institutes of Health. The government has certain rights in the invention.--

Signed and Sealed this
Sixth Day of February, 2018

Joseph Matal
*Performing the Functions and Duties of the
Under Secretary of Commerce for Intellectual Property and
Director of the United States Patent and Trademark Office*